United States Patent [19]

Shibata et al.

[11] 4,374,284

[45] Feb. 15, 1983

[54] ANTIULCER, ANTIINFLAMMATORY, AND ANTIALLERGIC AGENT COMPRISING AS THE MAIN INGREDIENT OLEAN-12-ENE-3$\beta$, 30-DIOL WHICH IS DEVOID OF SIDE EFFECTS OF GLYCYRRHETINIC ACID AND A NEW PROCESS FOR PREPARATION OF OLEAN-12-ENE-3$\beta$, 30-DIOL

[75] Inventors: Shoji Shibata, Tokyo; Akira Kumagai, Chiba; Masatoshi Harada, Tokyo; Singo Yano, Chiba; Hiroshi Saito, Tokyo; Kunio Takahashi, Urawa, all of Japan

[73] Assignee: Minophagen Pharmaceutical Company, Japan

[21] Appl. No.: 248,222

[22] Filed: Mar. 27, 1981

[30] Foreign Application Priority Data

Apr. 1, 1980 [JP] Japan .................................. 55-041196
Oct. 24, 1980 [JP] Japan .................................. 55-148412

[51] Int. Cl.³ ............................................. C07C 35/22
[52] U.S. Cl. ................................. 568/817; 568/714; 424/343
[58] Field of Search ................ 568/714, 817; 424/343

[56] References Cited

U.S. PATENT DOCUMENTS

| 2,146,897 | 2/1939  | Humphrey      | 568/714 |
| 2,744,101 | 5/1956  | Sublusky      | 568/714 |
| 2,817,677 | 12/1957 | Sublusky      | 568/714 |
| 3,523,139 | 8/1970  | Parkin et al. | 568/714 |

FOREIGN PATENT DOCUMENTS 524330  4/1956  Canada .............................. 568/714

OTHER PUBLICATIONS

Conanica et al., "Gazz. Chim. Ital.", vol 97, p. 1347, (1967).
Ryabinin et al., "Obshch. Kim", vol. 32, p. 644, (1962).
Conanica et al., "Gazz. Chim. Ital.", vol. 96, pp. 833–850, (1966).

*Primary Examiner*—Werren B. Lone
*Attorney, Agent, or Firm*—Robert E. Burns; Emmanuel J. Lobato; Bruce L. Adams

[57] ABSTRACT

This invention relates to an antiulcer, antiinflammatory, and antiallergic agent comprising as the main ingredient olean-12-ene-3$\beta$, 30-diol which is devoid of side effects of glycyrrhetinic acid and a process for preparation of olean-12-ene-3$\beta$, 30-diol.

17 Claims, No Drawings

ANTIULCER, ANTIINFLAMMATORY, AND ANTIALLERGIC AGENT COMPRISING AS THE MAIN INGREDIENT OLEAN-12-ENE-3β, 30-DIOL WHICH IS DEVOID OF SIDE EFFECTS OF GLYCYRRHETINIC ACID AND A NEW PROCESS FOR PREPARATION OF OLEAN-12-ENE-3β, 30-DIOL

BACKGROUND OF THE INVENTION

Glycyrrhizin, a saponin of licorice root, its aglycone, glycyrrhetinic acid, and their soluble derivatives have an excellent antiinflammatory effect, and their pharmacological effects as medicines for peptic ulcer and allergic disorders have been highly evaluated clinically. However, their administration in higher dosages for a long period results in so-called pseudoaldosteronism such as hypertension, hypopotassemia, and edema owing to abnormal metabolism of electrolytes. Therefore, the use of these medicines is regulated in the amounts to be administered.

The present inventors, Shibata, Kumagai and others, assumed that the foregoing aldosterone-like action (side effect) of glycyrrhetinic acid is ascribable to the fact that glycyrrhetinic acid inhibits the activity of $\Delta^4$-5α and 6β-reductase, which performs metabolism of aldosterone in the liver, leading to enhancement of the activity of aldosterone; thus, the present inventors have made assiduous investigations in order to obtain a compound which can reduce or remove the aldosterone-like action (side effect) of glycyrrhetinic acid and yet retain or enhance characteristic physiological activities of glycyrrhetinic acid. The present inventors have now found that olean-12-ene-3β, 30-diol is the most appropriate as a compound which can achieve the objective. Accordingly, this compound olean-12-ene-3β, 30-diol is devoid of side effects of glycyrrhetinic acid and yet shows excellent results, as seen from experimental results in examples (B, C, and D) hereinafter provided, in tests for antiulcer, antiinflammatory, and antiallergic activities. The preparation of the compound olean-12-ene-3β, 30-diol, has been described by L. Canonica et al.; Gazz. Chim. Ital., 97, 1347 (1967) and by Ryabinin and Konovalova Zh. Obshch. Khim. 32, 644 (1962). Such a process is shown in Chart 1.

chart 1
44-11

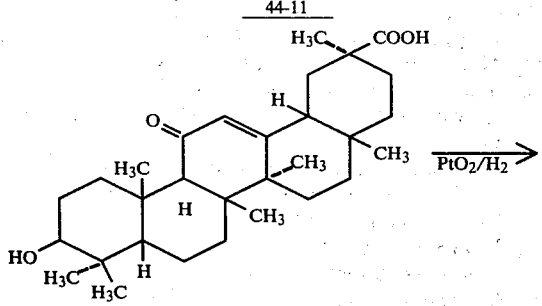

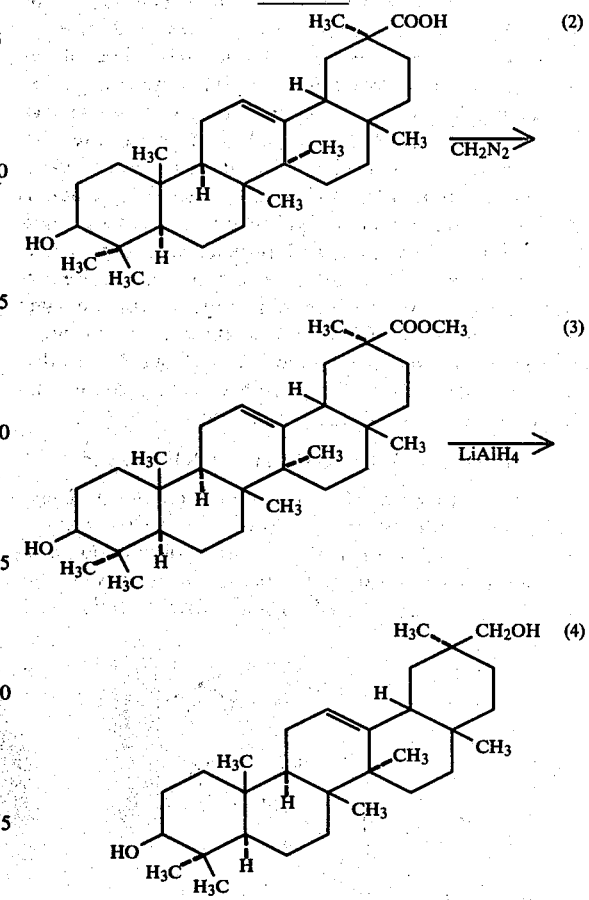

The process shown in Chart 1 involves complicated steps in which expensive platinum oxide is used. Further, in the process, an unchanged starting material is incorporated in intermediates to make the separation and purification of the intermediates difficult and hence the yield thereof is low. Therefore, the process is scarcely feasible and suffers from a great disadvantage that mass production is impossible. The present inventors have made assiduous investigations in order to remove these drawbacks of the known process. As a result, the present inventors have now succeeded in developing a new and useful process which satisfactorily meets requirements for industrial mass production, that is, a process in which production steps are simple and safe, and the production cost is low.

SUMMARY OF THE INVENTION

The primary object of the present invention is to obtain a remedy which is devoid of a side effect of glycyrrhetinic acid called pseudoaldosteronism and yet has excellent antiulcer, antiinflammatory, and antiallergic activities, although it has been known that glycyrrhetinic acid, its derivatives, and its salts have beneficial clinical effects against peptic ulcer, inflammation, and allergy, developing, however, pseudoaldosteronism on their long-term administration. As a result of our extensive experiments and investigations, we have been able to find that a compound olean-12-ene-3β, 30-diol is the most appropriate as a remedy meeting these requirements.

Another object of the present invention is to provide a useful industrial process for safely mass-producing the compound olean-12-ene-3β, 30-diol described above which is devoid of side effects of glycyrrhetinic acid by production steps much simpler than those of the known method shown in Chart 1 in high yield and at low cost.

The present inventors could confirm excellent effects of this compound olean-12-ene-3β, 30-diol, which is devoid of side effects of glycyrrhetinic acid, as an antiulcer, antiinflammatory, and antiallergic agent by several experiments hereinafter described which were carried out to attain the foregoing objects. At the same time, a new and useful process of the present invention for producing the compound olean-12-ene-3β, 30-diol devoid of side effects of glycyrrhetinic acid can be said to be desirable as an industrial process.

DESCRIPTION OF THE INVENTION

In order to know that the compound olean-12-ene-3β, 30-diol will not produce primary aldosteronism or administration, the present inventors took the following measures: To begin with, the present inventors synthesized three compounds of the following formula:

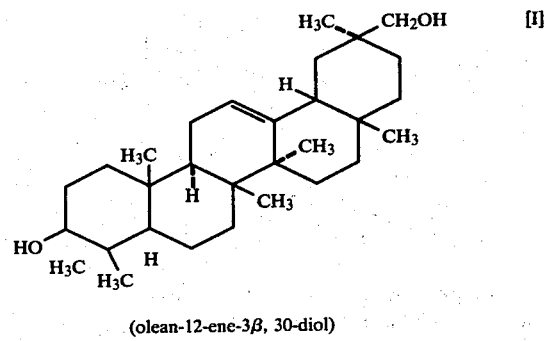

(olean-12-ene-3β, 30-diol)

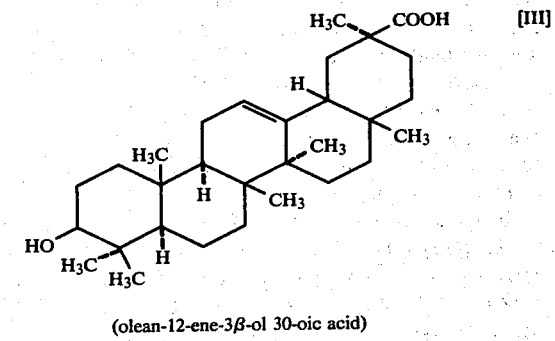

(olean-12-ene-3β-ol 30-oic acid)

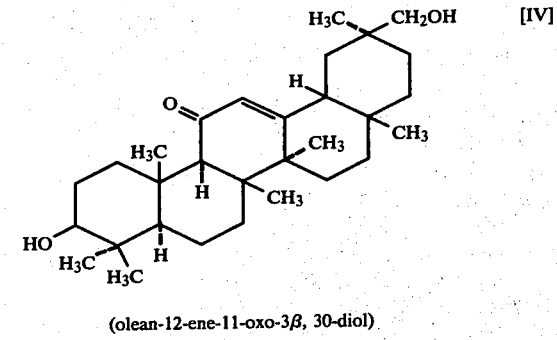

(olean-12-ene-11-oxo-3β, 30-diol)

By variously modifying glycyrrhetinic acid (olean-12-ene-11-oxo-3β-ol-30-oic acid) of the formula:

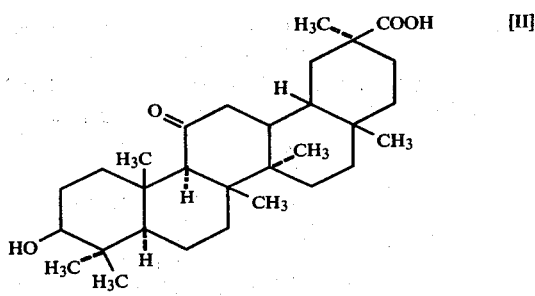

The compounds (I), (II), (III), and (IV) described above were investigated as to their effects upon $\Delta^4$-5α-5β-reductase which metabolizes aldosterone in the liver. As a result, whereas glycyrrhetinic acid (II) strongly inhibited the activity of the reductase, olean-12-ene-3β, 30-diol (I) which had been obtained by modifying the 11- and 30- positions of glycyrrhetinic acid (II) by reduction showed no inhibitory activity against 5α,5β-reductase in the liver. Consequently olean-12-ene-3β, 30-diol (I) would have no effect in developing primary aldosteronism, which is usually induced by the long-term and high dosage administration of glycyrrhetinic acid (the experimental results will be shown hereinafter in Experiment A). The compound olean-12-ene-3β, 30-diol devoid of a side effect such as aldosteronism, is useful as a remedy having excellent antiulcer, antiinflammatory, and antiallergic activities; these pharmacological effects will be explained in detail successively below by citing experimental results (Experiment B, C, and D).

First, experimental results that olean-12-ene-3β, 30-diol do not cause the syndrome of primary aldosteronism which is induced on long-term and higher dosage administration of glycyrrhetinic acid will be explained below by citing Experiment A.

Experiment A (inhibitory action on reductase)

In vitro experimental results regarding effects of glycyrrhetinic acid (II) and its modified compounds (III), (IV), and (I) on $\Delta^4$-5α and 5β-reductase for aldosterone in rat liver will be shown below.

Assay for activity of $\Delta^4$-5α and 5β-reductase (1) Preparation of enzyme solutions Rat livers were perfused with saline and excised to prepare a 25% or 50% homogenate with a solution of 0.25 M sucrose and 1 mM EDTA. The homogenate was spun at 10,000 g for 20 minutes to separate supernatant, which was centrifuged again at 105,000 g to obtain $\Delta^4$-5β-reductase as the supernatant. The pellet was appropriately diluted with a solution of 0.25 M sucrose-1 mM EDTA to use as a 5α-reductase solution.

(2) Conditions for incubation and assay

① Aldosterone ... 0.173 μM/0.05 ml ethanol solution

② Glycyrrhetinic acid or its modified compounds . ... 0.173 μM/0.05 ml ethanol solution Control ... 0.05 ml ethanol solution ③ Enzyme solution
5α-reductase solution 0.1 ml
5β-reductase solution 0.1 ml or 0.2 ml ④ NADPH$_2$ 2 mg ⑤ Phosphate buffer (0.1 M, pH 7.2) 1 ml
⑥ Distilled water The components ①, ②, ③, ④, ⑤, and ⑥ mentioned above were mixed to bring the total volume up to 2.5 ml. The mixture was incubated at 37° C. for 20 minutes. Before the incubation, however, 1 ml aliquot was removed from 2.5 ml of the mixture mentioned above and extracted with 5 ml of methylene dichloride. After the incubation, the remaining 1.5 ml was extracted with 5 ml of methylene dichloride. The optical density of the two methylene dichloride solutions prepared before and after the incubation was measured by a spectrophotometer (Hitachi) at 240 m$\mu$. Inhibition % of $\Delta^4$-5$\alpha$ and 5$\beta$-reductase activity was calculated from the difference in the optical density. The experimental results are as follows:

| | Experimental Results | |
|---|---|---|
| | enzyme | |
| compound | 5$\alpha$-reductase (inhibition %) | 5$\beta$-reductase (inhibition %) |
| control | 0 ± 2.5% | 0 + 3.4% |
| [II] | 9.2 + 2.2% (n.s) | 87.7 ± 2.2% (p < 0.001) |
| [III] | −0.5 ± 6.6% (n.s) | 20.5 + 4.1% (p < 0.01) |
| [IV] | 26.5 ± 5.6% (p < 0.001) | 88.4 + 4.7% (p < 0.001) |
| [I] | −7.1 + 2.2% (n.s) | 0 ± 1.1% (n.s) |

The molar ratios of aldosterone to glycyrrhetinic acid and its modified compounds were equal. Aldosterone was used as a substrate.
(II) olean-12-ene-11-oxo-3$\beta$-ol-30-oic acid
(III) olean-12-ene-3$\beta$-ol-30-oic acid
(IV) olean-12-ene-11-oxo-3$\beta$, 30-diol
(I) olean-12-ene-3$\beta$, 30-diol Next, experiments on the antiulcer activity of olean-12-ene-3$\beta$, 30-diol (I) of the present invention as compared with that of glycyrrhetinic acid (II) will be shown below as Experiment B (antiulcer activity).

Experiment B (antiulcer activity)

The following experiments were carried out with respect to antiulcer activity of olean-12-ene-3$\beta$, 30-diol (I) of the present invention as compared with that of glycyrrhetinic acid.

(a) Mice Experiments on stress-induced ulcer Experimental procedures:

Male ddY mice weighing about 20 g were made to fast for 18 hours. Water was given freely. Compounds to be tested were suspended in Tween 80 to prepare an aqueous suspension and administered orally. Immediately thereafter, the mice were subjected to restraint plus water immersion stress (25° C.) for 6 hours. Thereafter, the stomach was excised and fixed by formalin. The degree of ulcer was shown as a total of the length. The control group was given only the solvent.

Experimental results were as follows:

| | Inhibitory Effect on Ulcer | | | |
|---|---|---|---|---|
| compound | number of animals | dose mg/kg (p.o.) | ulcer index | p |
| control | 8 | | 5.63 ± 0.55 | |
| (I) | 8 | 200 | 2.94 ± 0.81 | <0.05 |
| control | 8 | | 4.13 ± 0.8 | |
| (I) | 8 | 200 | 2.19 ± 0.6 | |
| control | 8 | | 6.00 ± 0.87 | |
| (I) | 8 | 200 | 3.88 ± 0.79 | <0.10 |
| (II) | 8 | 200 | 4.00 ± 1.07 | |
| control | 10 | | 4.20 ± 0.70 | |
| (I) | 9 | 200 | 1.89 ± 0.53 | <0.05 |
| (II) | 9 | 200 | 3.11 ± 0.63 | |
| control | 8 | | 4.13 ± 0.53 | |
| (II) | 8 | 200 | 2.39 ± 1.14 | |
| (III) | 8 | 200 | 3.38 ± 0.79 | |

(b) Rat experiment on aspirin-induced ulcer
(a) Experimental procedures:

Male Wister rats weighing about 220 g were made to fast for 24 hours. Water was given freely. The rats were laparotomized under anesthesia with ether. The stomach was drawn out and ligated at the pylorus. Immediately thereafter, 1% CMC suspension of aspirin was administered orally in a dose of 100 mg/kg/5 ml. Aqueous suspensions of compounds to be tested were prepared in the same manner as in the experiment (a) and administered intraduodenally at the same time. The wound was closed and the rats were set free. After 7 hours, the stomach was excised and ulcer was measured in the same manner as in the experiment (a).

| | Experimental results Inhibitory Effect | | | |
|---|---|---|---|---|
| compounds | number of animals | doses mg/kg p.o. | ulcer index | p |
| control | 5 | | 14.1 ± 3.14 | |
| II | 5 | 320 | 13.3 ± 3.99 | |
| I | 5 | 320 | 6.2 ± 2.37 | <0.10 |

(b) Experimental procedures:

Male Wister rats weighing 120–140 g were made to fast for 24 hours, and compounds to be tested were administered orally. After 5 hours, the rats were killed by a blow. The stomach was excised and observed for the presence of ulcer.

The size of ulcer was measured by ulcer index (ulcer length × width mm$^2$).

| | Experimental results Inhibitory Effect | | |
|---|---|---|---|
| compounds | number of animals | doses mg/kg (p.o.) | ulcer index |
| control | 7 | | 0 |
| aspirin | 7 | 200 | 7.11 ± 1.1 |
| [I] | 8 | 200 | 0 |
| aspirin + [I] | 4 | 200 + 200 | 3.6 ± 0.3 |

(c) Experiments with rats on ulcers induced by acetic acid

Chronic gastric ulcers were induced by penetrating 100% acetic acid serosally into gastric wall for 60 sec. using a small cup (6 mm in diameter, 5 mm in height).

From the next day, compounds to be tested were administered orally twice a day (morning and evening) for 14 days. Autopsies were carried out 15 days after the administrations.

| compound | Dose mg/kg (half dose twice/day) | ulcer value (major axis × minor axis) | | |
|---|---|---|---|---|
| | | Experiment 1 | Experiment 2 | Total |
| control | | 12.0 ± 2.3 | 8.9 ± 1.7 | 10.4 ± 1.4 |

-continued

| compound | Dose mg/kg (half dose twice/day) | ulcer value (major axis × minor axis) | | |
|---|---|---|---|---|
| | | Experiment 1 | Experiment 2 | Total |
| II | 200 | (7)<br>10.4 ± 2.7 | (8)<br>11.5 ± 2.2 | (15)<br>10.9 ± 1.7 |
| | 400 | (7)<br>8.6 ± 2.2 | (7)<br>5.8 ± 1.0 | (14)<br>7.1 ± 1.2 |
| I | 200 | (6)<br>10.1 ± 3.4 | (7)<br>6.7 ± 2.2 | (13)<br>8.4 ± 2.0 |
| | 400 | (7)<br>7.5 ± 0.7 | (7)<br>5.2 ± 1.2 | (14)<br>6.2 ± 0.8* |
| | | (6) | (8) | (14) |

( ) . . . number of animals
*$p < 0.05$

Findings from Experiment B (a) The following effects were observed as inhibitory activities against ① Glycyrrhetinic acid (II) showed the inhibitory effect in a dose of 200 mg/kg.

② The present compound olean-12-ene-3β, 30-diol (I) showed a stronger inhibitory effect than glycyrrhetinic acid (II).

③ Olean-12-ene-3β-ol 30-oic acid (III) of which only the 11-position had been reduced showed the effect in a dose of 200 mg/kg as with glycyrrhetinic acid (II).

(b) The following effects were observed as an inhibitory activity against aspirin-induced ulcer in rats.

In the experiment (a), whereas the present compound olean-12-ene-3β, 30-diol (I) showed an inhibitory effect, glycyrrhetinic acid (II) scarcely showed the effect.

In the experiment (b), olean-12-ene-3β, 30-diol (I) did not produce ulcer and inhibited the development of ulcer induced by aspirin.

(c) The following results were obtained as a result of experiments with rats on ulcers induced by acetic acid:

The inhibitory effects of olean-12-ene-3β, 30-diol [I] and glycyrrhetinic acid [II] were examined. At a dose of 200 mg, [I] showed an inhibitory effect to some extent. At an increased dose of 400 mg, however, both [I] and [II] clearly showed inhibitory effects; in particular, the effect of [I] is remarkable as compared with that of [II], the healing rate of [I] being more than 40%.

Those experiments described above on antiulcer activities consisting of experiments on ulcers induced by (a) stress and by chemicals (b) and (c) have revealed that the present compound olean-12-ene-3β, 30-diol [I], as was expected by the present inventors, shows superior effects to glycyrrhetinic acid in all the experiments.

Next, experiments on the antiinflammatory and analgesic activities of the present compound olean-12-ene-3β, 30-diol (I) will be explained below by citing Experiment C.

Experiment C (antiinflammatory and analgesic action)

(a) Test on rat paw induced with carrageenin

To the plantar side of the hind paw of male Wister rats was administered subcutaneously 0.05 ml/rat of 10% saline solution of carrageenin. Edema after three hours was measured by the volume method and the rate of inhibition was assayed. Compounds were administered orally 30 minutes before administration of carrageenin.

$$\text{the rate of edema} = \frac{\text{(foot volume after administration of inflammation-inducing substance)} - \text{(foot volume before administration of inflammation-inducing substance)}}{\text{foot volume before administration of inflammation-inducing substance}}$$

$$\text{the rate of inhibition} = \frac{\text{control edema rate} - \text{edema rate due to a drug}}{\text{control edema rate}}$$

Experimental results: Edema-inhibitory effect

| compound | number of animals | doses mg/kg p.o. | edema % | inhibition % |
|---|---|---|---|---|
| control | 4 | | 71 ± 6 | 0 |
| aspirin | 4 | 200 | 17 ± 3 | 76.1 |
| [I] | 4 | 200 | 52 ± 5 | 26.8 |
| [I] + aspirin | 4 | 200 + 200 | 19 ± 4 | 73.2 |

(b) Effect on writhing induced by acetic acid (analgesic action)

Experimental procedures:

The present compound olean-12-ene-3β, 30-diol (I) was administered orally to male ddY mice weighing 25-27 g. After 30 minutes, saline containing 0.7% acetic acid was administered intraperitoneally. The number of writhings of the mice was counted for 10 minutes from, 10 min. of the administration. Aspirin was used as the reference.

Experimental results

| compounds | number of animals | doses mg/kg (p.o.) | number of writhing |
|---|---|---|---|
| control | 8 | | 24.9 ± 1.6 |
| aspirin | 8 | 200 | 0** |
| [I] | 8 | 100 | 15.5 ± 2.8** |
| | 8 | 200 | 11.1 ± 1.6** |
| | 8 | 400 | 8.0 ± 1.7** |
| [II] | 8 | 100 | 12.2 ± 3.5 |
| | 8 | 200 | 15.2 ± 3.6 |
| | 8 | 400 | 11.7 ± 2.9** |

**$p < 0.01$

Findings from Experiment C (a) The present compound olean-12-ene-3β, 30-diol (I) has an inhibitory activity against inflammation, but the activity is inferior to that of aspirin. When used in combination with aspirin, the compound will not affect the inhibitory activity of aspirin.

(b) Writhing reaction induced by acetic acid (analgesic action):

Increasing doses of both the present compound olean-12-ene-3β, 30-diol (I) and glycyrrhetinic acid (II) significantly decrease the number of writhing induced by acetic acid. The activity of (I) is a little stronger than that of (II), but not so perfect as aspirin.

Next, the antiallergic activity of the present compound olean-12-ene-3β, 30-diol (I) will be shown below by citing Experiment D.

Experiment D (antiallergic activity)

(a) PCA—Test (type I allergy)
Experimental procedures:

Male Wister rats weighing 200-140 g were shaved at the abdomen. After 24 hours, 0.05 ml of serum diluted with saline (Blood samples were diluted to 1/32 and 1/64; The blood samples were collected from rats 3 weeks after administration of pertussis vaccine and egg albumin.) was injected intradermally at the abdomen. After 48 hours, compounds to be tested were administered intraperitoneally. Two hours thereafter, 0.5 ml./100 g of a solution of antigen and pigment (a solution of 0.4% egg albumin and 0.5% Pontamine sky blue) was administered. After 45 minutes, the rats were decapitated and bled, and the diameter of the pigment-leaking site under the skin was measured to obtain the area.

| compound | number of animals | doses mg/kg (intraperitoneally) | area (mm$^2$) (inhibition %) 1/32 | 1/64 |
|---|---|---|---|---|
| control | 5 | | 35.2 ± 5.3 | 16.4 ± 2.8 |
| [II] | 5 | 200 | 25.2 ± 6.6 (71.6%) | 7.7 ± 6.5 (46.9%) |
| [I] | 5 | 100 | 22.3 ± 9.1 (63.4%) | 6.8 ± 4.6 (41.5%) |
| | 5 | 200 | — | 6.3 ± 4.8 (38.4%)) |

(b) Arthus phenomenon test (type III allergy)
Experimental procedures:

To the back part of female guinea pig weighing 250–300 g, 10 mg/kg of egg albumin was administered subcutaneously. After 21 days, 2 mg/kg of egg albumin was administered intravenously, whereby death of the guinea pig due to anaphylactic shock was recognized to confirm establishment of sensitization. Thirty minutes after compounds to be tested were administered intraperitoneally, 0, 10, 100, 1000 μg/0.1 ml of egg albumin were each administered to the abdominal part which had been shaved. After 12 hours, the abdominal part was observed to obtain the area of the site of internal hemorrhage.

| compounds | number of animals | doses mg/kg (intraperitoneally) | Experimental Results area mm$^2$ (inhibition %) 10 | 100 | 1000 μg/ 0.1 ml |
|---|---|---|---|---|---|
| control | 4 | | 0 | 110 ± 67 (100) | 409 ± 130 (100) |
| [I] | 4 | 100 | 0 | 98 ± 98 (89.1) | 334 ± 174 (81.7) |
| [I] | 4 | 200 | 0 | 30 ± 30 (27.3) | 76 ± 62 (18.6) |

Findings from Experiment D (antiallergic activity)

(a) PCA reaction (type I allergy)

When diluted to 1/64, both of the present compound olean-12-ene-3β, 30-diol (I) and glycyrrhetinic acid (II) showed an inhibition rate of less than 50%. The activity of (I) is a little stronger than that of (II).

(b) Arthus phenomenon test (type III allergy)

Concerning the inhibition rate of Arthus phenomenon, it was observed that internal hemorrhage was obviously prevented to the extent of 27.3% and 18.6% by administration of 200 mg/kg of compounds to be tested.

As described above, the present compound olean-12-3β, 30-diol (I), which is obtained by reductively modifying the 11- and 30-positions of glycyrrhetinic acid (II), is entirely devoid of aldosterone-like action of glycyrrhetinic acid; further, as can be seen from pharmacological activities in Experiment B, C, and D described above, the compound nonetheless retains an antiulcer activity characteristic of glycyrrhetinic acid and even tends to enhance the antiulcer activity. The present compound also shows antiinflammatory and antiallergic activities to such an extent as to fulfil the present inventors' expectations.

Acute toxicity test

Acute toxicity test of glycyrrhetinic acid (II) and olean-12-ene-3β, 30-diol (I) in mice by oral and intraperitoneal administration Method To male mice (ddY) weighing 24 g–26 g, 10 mice in one group, compounds to be tested (suspended in Tween 80) in various doses of the ratio (1, 2) were administered (orally and intraperitoneally), and LD$_{50}$ was determined by the Litchfield-Wilcoxon method.

Results

Glycyrrhetinic acid (II)
  Oral administration LD$_{50}$=560 mg/kg
  Confidence limit 518–605 mg/kg P<0.05
  Intraperitoneal administration LD$_{50}$=455 mg/kg
  Confidence limit 433–478 mg/kg P<0.05
Olean-12-ene-3β, 30-diol [I]
  Oral administration LD$_{50}$>5 g/kg
  Intraperitoneal administration LD$_{50}$>4 g/kg
  Survival and death were confirmed 48 hours and one weak after the administration, but there was no difference.

The foregoing results show that olean-12-ene-3β, 30-diol (I) has very low toxicity.

The compound of this Invention, olean-12-ene-3β, 30-diol form the following esters with organic acids and inorganic acids which are also within the scope of the Invention.

These esters are more soluble in water than olean-12-ene-3β, 30-diol.

① Succinic acid ester of olean-12-ene-3β, 30-diol
  (a) 3-O-hemisuccinate and its alkali-salts.
  (b) 3,30-O-dihemisuccinate and its alkali-salts.
② Phosphoric acid ester of olean-12-ene-3β, 30-diol
  (a) 3-O-phosphate and its dialkali salt.
③ Sulfuric acid ester of olean-12-ene-3β, 30-diol
  (a) 3-O-sulfate and its alkali-salt.
  (b) 3,30-disulfate and its dialkali salts.

Those compounds are preferably administered orally, but parenteral routes, topical treatment can also be employed.

Suitable forms for oral administration include liquids (such as polyethylene glycol solutions), tablets, solid suspensions and capsules.

The daily dose for an adult is generally about 0.6 to 20 milligrams per kilogram of body weight in oral administration, and about 30 to about 1,000 milligrams per day in oral administration calculated on the body weight of the adult as 50 kilograms.

The present compound olean-12-ene-3β, 30-diol has been found to fulfil the present inventors' expectations as a result of pharmacological experiments with several compounds synthesized by modifying glycyrrhetinic acid as described at the outset of the detailed description of the invention in the specification; however, the olean-12-ene-3β, 30-diol used in these pharmacological experiments was synthesized according to the known method described in the literature (L. Canonica et al.; Gazz. Chim. Ital. 96, 833 (1966) and 97, 86 (1977)), so the method will be shown below as an example.

(1) Method for obtaining olean-12-ene-3β-ol-30-oic acid (III)

In 20 ml of acetic acid was added 2.4 g of platinum oxide, and the mixture was stirred with hydrogen in a stirring-type hydrogenation apparatus for 30 minutes. To the suspension of platinum oxide was added 170 ml of acetic acid containing 4.0 g of glycyrrhetinic acid, and the mixture was subjected to reduction with stirring at room temperature and atmospheric pressure for about 8 hours to obtain a precipitate of olean-12-ene-3β-ol-30-oic acid. To the reaction mixture was added 100 ml of acetic acid, and the mixture was heated on a water bath. Insoluble platinum was removed, the acetic acid distilled off, and the residue recrystallized repeatedly from acetic acid to give olean-12-ene-3β-ol-30-oic acid. The yield was 80%.

(2) Method for obtaining the desired compound from olean-12-ene-3β-ol-30-oic acid Into 300 ml of chloroform was dissolved 4.5 g of olean-12-ene-3β-ol-30-oic acid obtained in (1) described above. To the solution was added a large excess of an ethereal solution of diazomethane. After 30 minutes, the solvent was evaporated and dried at 60° C. under reduced pressure for 1 hour to yield crystals. The crystals were dissolved in 100 ml of tetrahydrofuran. The solution was added gradually to a solution of lithium aluminum hydride (0.36 g) in 300 ml of tetrahydrofuran and stirred for 1 hour. After the aluminum complex in this solution was decomposed with 20 ml of methanol and 20 ml of water, the solution was filtered, the filtrate neutralized with hydrochloric acid. To the solution were added 400 ml of water and 400 ml of chloroform, and the solution was extracted three times. The chloroform layer was washed three times with water and dried over sodium sulfate for 6 hours. After the solvent was evaporated, the residue was separated by silica gel column using chloroform-methanol as developing solvent to obtain the desired olean-12-ene-3β, 30-diol. The yield was 68.3%.

Next, the second object of the present invention, that is, a new and useful process for preparation of olean-12-ene-3β, 30-diol of the following formula:

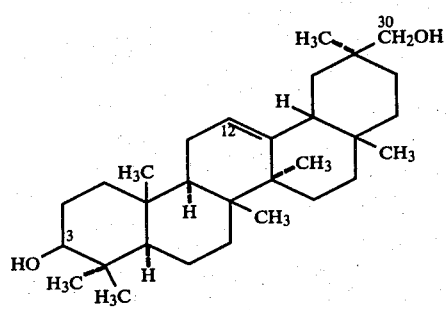

will be explained in detail below.

The gist of the new process for preparation of olean-12-ene-3β, 30-diol is characterized in that glycyrrhetinic acid (olean-12-ene-11-oxo-3β-ol-30-oic acid) is reduced to the triol compound (olean-12-ene-3β, 11ξ, 30-triol), then the triol compound obtained is catalytically reduced to obtain the desired product. There are two methods for reducing the starting material glycyrrhetinic acid to the triol compound; that is, in one method, the reduction is conducted directly using an alkali aluminum or alkali boron complex of the formula

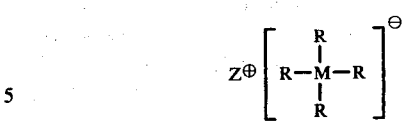

wherein: Z is an alkali metal; M is boron or Al; and each R is H or $OR^1$, $R^1$ being an aliphatic group, such as sodium bis (2-methoxyethoxy)-aluminum hydride as the reducing agent; in another method, —COOH of glycyrrhetinic acid is converted into —$COOCH_3$ with an ethereal solution of diazomethane, then reduced with lithium aluminum hydride.

Next, a new and the most preferable manufacturing process of the present invention will be shown in Chart 2.

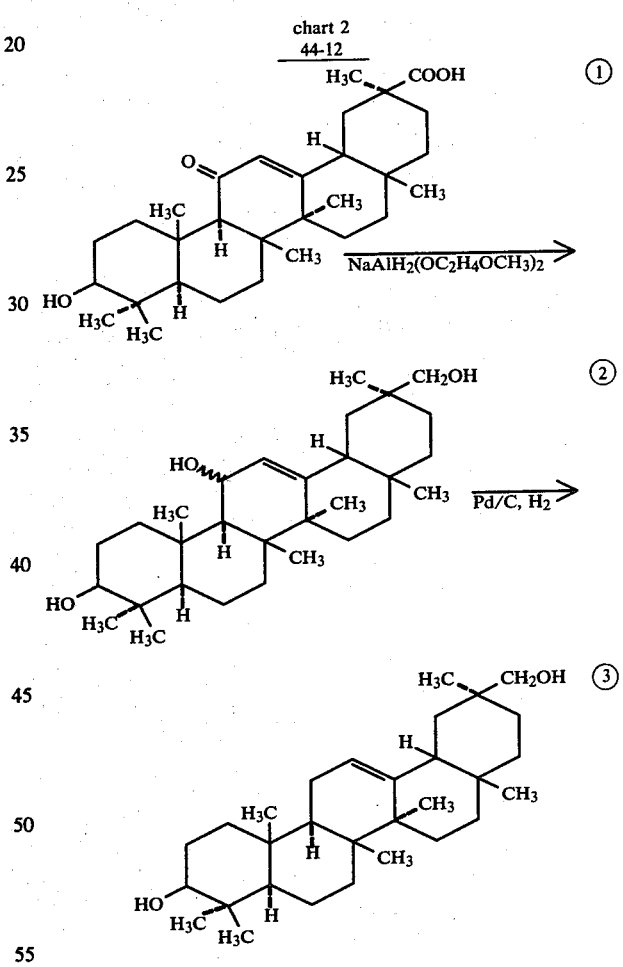

The process shown in Chart 2 is a process described is Example [1] hereinafter provided, in which process glycyrrhetinic acid ① is dissolved in tetrahydrofuran and directly reduced with sodium bis (2-methoxyethoxy)aluminum hydride to produce the triol compound ②, which is then dissolved in ethanol and catalytically reduced with inexpensive Pd-C to obtain the desired olean-12-ene-3β, 30-diol ③. This process can be said to be the most preferable industrial process applicable to mass production since the steps are very simple and safely conducted affording a high overall yield of at least more than 86%.

Next, the other method concerning the first step of the process of the present invention, that is, a step in which glycyrrhetinic acid is reduced to the triol compound will be explained. In the step, —COOH of glycyrrhetinic acid ① is converted into —COOCH₃ ①' with an ethereal solution of diazomethane, then the resulting product is reduced with lithium aluminum hydride in tetrahydrofuran as a solvent to afford the triol compound ②. The succeeding process is the same as the foregoing method; that is, the triol compound is catalytically reduced with inexpensive Pd-C to produce the desired compound of the present invention ③. This process will be shown in Chart 3.

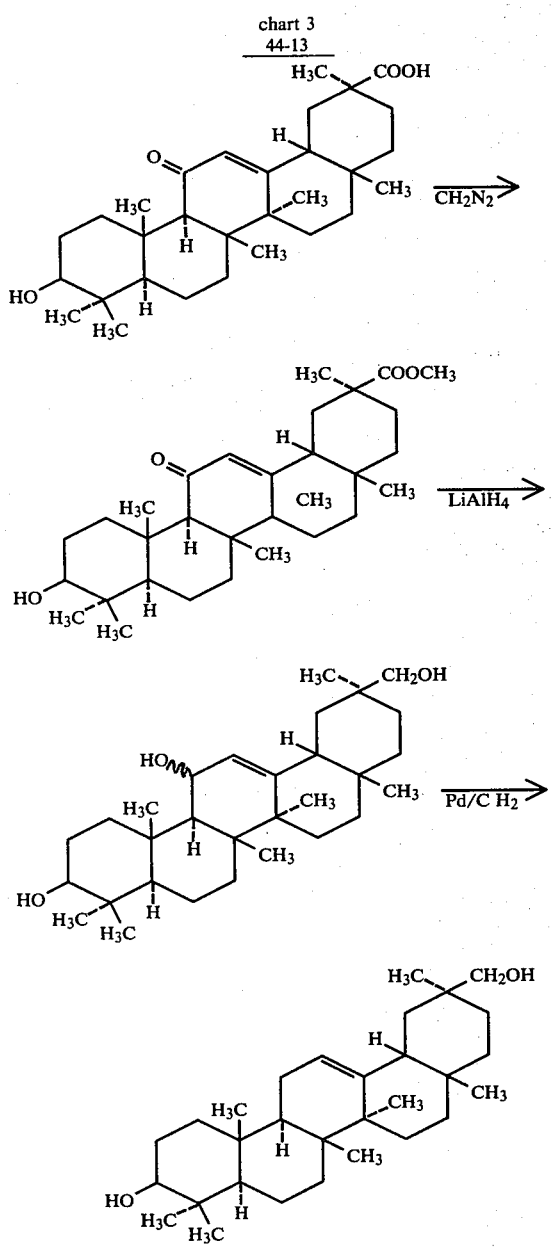

chart 3
44-13

This process is inferior to the process shown in Chart 2 in that reduction cannot be carried out directly, an additional step being required in which —COOH is converted into —COOCH₃. This process corresponds to Example (2) hereinafter provided and gives an overall yield of 62%, which is significantly higher than 53% of the known method.

Next, examples will be provided each for processes shown in Chart 2 and 3 as new processes for producing olean-12-ene-3β, 30-diol of the present invention.

EXAMPLE [1] (Process shown in Chart 2)

In a three neck 300 ml-flask equipped with a sealed stirrer, a reflux condenser fitted with a drying tube, and a dropping funnel with a side arm was placed 30 ml of dried tetrahydrofuran. Thereto was added 14.1 ml of a 70% toluene solution of sodium bis (2-methoxyethoxy)aluminum hydride. Then, to the mixture was gradually added 4.7 g of glycyrrhetinic acid dissolved in 40 ml of dried tetrahydrofuran from the dropping funnel with a side arm. After dropping, the mixture was refluxed for 1 hour and then cooled. Thereto was gradually added 10% hydrochloric acid, whereby the aluminum complex decomposed while foaming. The precipitate was removed by filtration, and 50 ml of water was added to the filtrate. The filtrate was extracted three times with 200 ml of chloroform. Combined chloroform layers were washed three times with 200 ml of water and dried over sodium sulfate (anhydrous) for 6 hours. The sodium sulfate was removed by filtration, and the solvent was evaporated at not more than 40° C. from the filtrate to afford a mixture mainly comprising the triol compound. The mixture, dissolved in 50 ml of ethanol, was stirred with 23 g of Pd-C (10%) and hydrogen in a stirring-type hydrogenation apparatus for 8 hours. The catalyst was removed by filtration, the solvent evaporated, and the residue separated by silica gel column using chloroform-methanol as developing solvent. The product was recrystallized from tetrahydrofuran to afford 3.81 g of crystalline white powders of olean-12-ene-3β, 30-diol.

EXAMPLE [2] (Process shown in Chart 3)

In chloroform was dissolved 4.7 g of glycyrrhetinic acid, and thereto was added an ethereal solution of diazomethane until the reaction mixture turned yellow. The solvent was evaporated, and the residue was dried at not more than 60° C. under reduced pressure. In a three neck 300 ml-flask equipped with a sealed stirrer, a reflux condenser fitted with a drying tube, and a dropping funnel with a side arm was placed 150 ml of dried tetrahydrofuran, and thereto was added 0.54 g of lithium aluminum hydride. Thereto was gradually added the methyl ester of glycyrrhetinic acid dissolved in 50 ml of dried tetrahydrofuran from the dropping funnel. After stirring for 1 hour, the aluminium complex was decomposed with 50 ml of methanol and 50 ml of water, and the resulting mixture was filtered. The filtrate, neutralized with 10% hydrochloric acid, was added with 200 ml of water, and extracted three times with 300 ml of chloroform. Combined chloroform layers were washed three times with 300 ml of water and dried over sodium sulfate (anhydrous) for 6 hours. The sodium sulfate was removed by filtration, and the solvent evaporated at not more than 40° C. to afford 3.91 g of a mixture mainly comprising the triol compound. The product was dissolved in 300 ml of ethanol and stirred with 10 g of Pd-C (10%) and hydrogen in a stirring-type hydrogenation apparatus for 8 hours. The catalyst was removed by filtration, the solvent evaporated, and the residue separated by silica gel column using chloroform-methanol as developing solvent. The product was recrystallized from tetrahydrofuran to afford 2.73 g of crystalline white powder of olean-12-ene-3β, 30-diol. The olean-12-ene-3β, 30-diol obtained in Example 1 and 2 has the following properties:

(1) Melting point 250°–251° C.
(2) IR spectrum (cm⁻¹)
3600–3050 (C₃-position, C₃₀-position ν-OH stretching vibration)
1630 (Δ12–13 νC=C)
(3) ¹³C nmr spectrum (Pyridine-d₅) δppm [TMS]
145.0 (C₍₁₃₎-), 123.5

(C₍₁₂₎-⌐⌐), 78.2 (C₍₃₎-OH), 66.0 (C₍₃₀₎-OH),
55.9 (C₍₅₎)
(4) Mass spectrum (m/e)

| M⁺ | Found | Calculated | |
|---|---|---|---|
| | 442.38 | 442.73 | C₃₀H₅₀O₂ |
| | 234.20 | 234.38 | C₁₆H₂₆O |

What is claimed is:

1. A pharmaceutical composition useful for the treatment of ulcer comprising as an active ingredient olean-12-ene-3β, 30-diol of the formula:

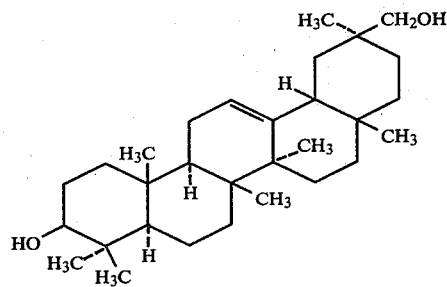

in an amount effective to display antiulcer activity in combination with a pharmaceutically acceptable carrier.

2. A method for treating ulcer comprising administering to a patient having ulcer the active compound olean-12-ene-3β, 30-diol of the formula

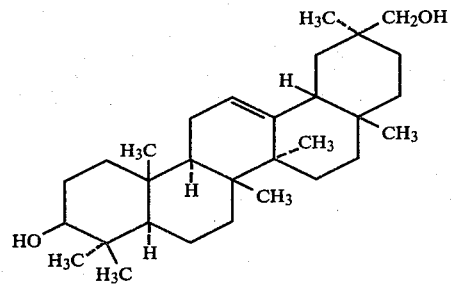

in an amount effective to control ulcer.

3. A method for treating inflammations which comprises administering to a patient having inflammation the active compound olean-12-ene-3β, 30-diol of the formula

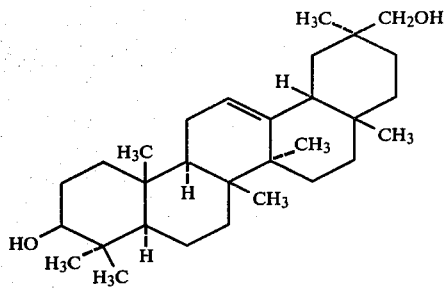

in an amount effective to control inflammation.

4. A method for treating allergy which comprises administering to a patent having allergy the active compound olean-12-ene-3β, 30-diol of the formula

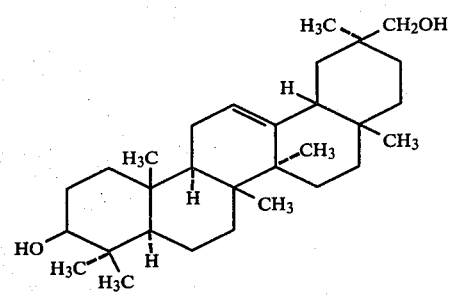

in an amount effective to control allergy.

5. A pharmaceutical composition useful for treatment of inflammation comprising as an active ingredient olean-12-ene-3β,30-diol

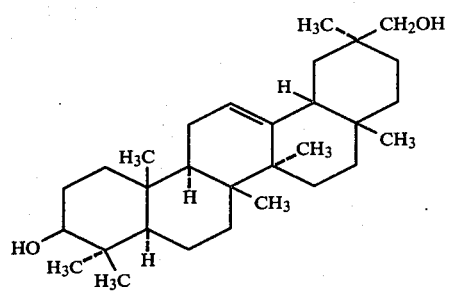

in an amount effective to display antiinflammatory activity in combination with a pharmaceutically acceptable carrier.

6. A pharmaceutical composition useful for the treatment of allergy comprising as the active ingredient olean-12-ene-3β,30-diol

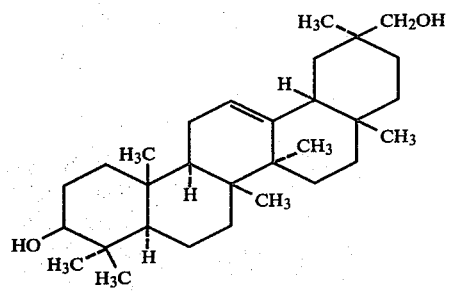

in an amount effective to display antiallergic activity, in combination with a pharmaceutically effective carrier.

7. The pharmaceutical composition according to claim 1, 5 or 6 in a form suitable for oral administration.

8. The method of treatment according to claim 2, 3 or 4 in which the active compound is administered as a composition comprising a pharmaceutically acceptable excipient.

9. The method of treatment according to claim 8 in which the active compound is administered orally.

10. The method of treatment according to claim 9 in which the active compound is administered in an amount of about 0.6 to 20 mg. per kilogram of body weight.

11. A process for preparation of olean-12-ene-3β, 30-diol of the formula:

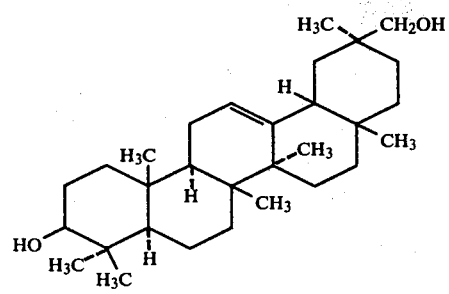

which comprises reducing glycyrrhetinic acid of the formula

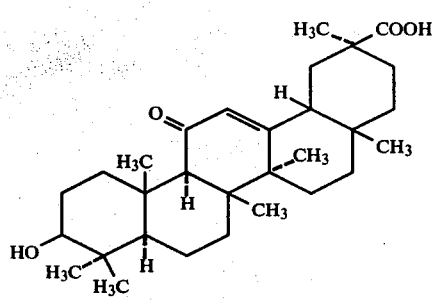

with an alkali aluminum or alkali boron complex of the formula

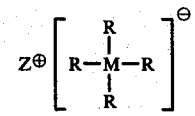

wherein Z is an alkali metal; M is boron or Al; and each R is H or $OR^1$, $R^1$ being an aliphatic group, to produce the corresponding triol, olean-12-ene-3β, 11ε, 30-triol and then catalytically reducing said triol with hydrogen gas in contact with a catalyst selected from palladium on charcoal a Raney nickel to produce olean-12-ene-3β, 30-diol.

12. The process according to claim 11, wherein glycyrrhetinic acid is directly reduced to the corresponding triol with sodium bis(2-methoxyethoxy)aluminum hydride and then the triol is catalytically reduced with hydrogen in contact with a Pd-C catalyst to produce olean-12-ene-3β-30-diol.

13. The process according to claim 11 wherein glycyrrhetinic acid is reduced by means of the complex sodium bis(2-methoxyethoxy)aluminum hydride.

14. The process according to claim 13 wherein the reduction of glycyrrhetinic acid is carried out in a solution of tetrahydrofuran.

15. The process according to claim 13 wherein the reduction of glycyrrhetinic acid is carried out in refluxing tetrahydrofuran.

16. The process according to claim 14 or 15 wherein the catalytic reduction of the triol is carried out with hydrogen and palladium on charcoal.

17. The process according to claim 16 wherein the catalytic reduction is carried out in ethanol solution with agitation.

* * * * *